US00PP16931P2

(12) United States Plant Patent
Tellwright

(10) Patent No.: US PP16,931 P2
(45) Date of Patent: Aug. 1, 2006

(54) ***NEMESIA* PLANT NAMED 'FLEURBAC'**

(50) Latin Name: *Nemesia×hybrida*
Varietal Denomination: Fleurbac

(76) Inventor: Martine Tellwright, Highground House, Highground Lane, Barnham, W Sussex (GB), PO22 0BU ( * ) Notice: Subject to any disclaimer, the term of this patent is extended or adjusted under 35 U.S.C. 154(b) by 31 days.

(21) Appl. No.: 11/138,003

(22) Filed: May 27, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—Louanne Krawczewicz Myers

(57) ABSTRACT

A new and distinct cultivar of *Nemesia* plant named 'Fleurbac' that is characterized by upright compact habit, medium-green leaves, large fragrant bicolor flowers, and two individual colors of bi-color flowers per individual plant. In combination these characteristics set 'Fleurbac' apart from all other existing varieties of *Nemesia* known to the inventor.

2 Drawing Sheets

Genus: *Nemesia.*
Species:×*hybrida.*
Denomination: Fleurbac.

BACKGROUND OF THE INVENTION

The present invention relates to a new and distinct cultivar of *Nemesia* plant that is grown as an ornamental for border, patio container or hanging basket. The new cultivar is known botanically as *Nemesia×hybrida* and will be referred to hereinafter by the cultivar name 'Fleurbac'. The new variety 'Fleurbac' sets few seeds, and exhibits upright compact habit, large fragrant bi-colored flowers, two differently colored bi-color flowers per individual plant, and medium-green leaves.

Fleurbac is a hybrid that resulted from a formal breeding program begun by the inventor in 1998 at her nursery in West Sussex, United Kingdom. The purpose of the breeding program is to produce new varieties of *Nemesia* that exhibit compact habit, new flower color and improved flower size.

The inventor conducted the first cross-pollination between the inventor's variety of *Nemesia* plant named 'Fleurame' (U.S. Plant patent application Ser. No. 11/095,139, filed Mar. 30, 2005) and the inventor's variety of *Nemesia* plant named 'Ice Blue' (unpatented). This cross-pollination process produced many seedlings from which the inventor selected the *Nemesia* seedling numbered by the inventor as 203 (unreleased, unpatented).

Secondly and separately, the inventor conducted the cross-pollination of *Nemesia* plant named 'Ice Blue' with *Nemesia* seedling 168, an unreleased and unpatented plant retained by the inventor from previous breeding cycles. *Nemesia* seedling 168 exhibits compact habit and scented mauve flowers with a yellow eye. From the many seedlings that resulted from this second cross-pollination, the inventor selected a hybrid *Nemesia* seedling 200, since named 'Celine' (unpatented).

Finally the inventor conducted the cross-pollination of *Nemesia* seedling 203 and *Nemesia* seedling 200. This cross-pollination produced a large number of seedlings from which the inventor selected the 'Fleurbac'. The female parent of 'Fleurbac' is *Nemesia* seedling 203 (unpatented) and the male parent of 'Fleurbac' is *Nemesia* seedling 200 (unpatented). The new variety 'Fleurbac' was selected by the inventor in 2002 in West Sussex, United Kingdom. The criteria used for selection, was large individual bi-colored flowers, upright compact habit, and two differently colored bi-color flowers per individual plant.

The closest comparison plant is the inventor's variety *Nemesia* 'Melanie' (unpatented) which exhibits bright pink flowers. 'Fleurbac' is distinguishable from the comparison plant 'Melanie' by flower colors. 'Fleurbac' is distinguishable from the female parent plant by upright compact habit, and two individual colors of bi-color flowers per individual plant. 'Fleurbac' is distinguishable from the male parent plant by bi-color flowers. The bi-color flower colors of the female parent *Nemesia* seedling 203 are mauve and pale pink, and the flower color of the male parent, *Nemesia* seedling 200 is cerise.

'Fleurbac' was first asexually propagated by the inventor in 2002 in a cultivated area of West Sussex, United Kingdom using softwood cuttings. The distinguishing characteristics of 'Fleurbac' have been determined stable and are reproduced true to type in successive generations.

SUMMARY OF THE INVENTION

The following traits have been repeatedly observed and represent the distinguishing characteristics of 'Fleurbac'. In combination these traits set the new cultivar apart from all other existing varieties of *Nemesia* known to the inventor. 'Fleurbac' has not been tested under all possible conditions and phenotypic differences may be observed with variations in environmental, climatic, and cultural conditions, however, without any variance in genotype.

1. *Nemesia×hybrida* 'Fleurbac' exhibits upright compact habit.
2. *Nemesia×hybrida* 'Fleurbac' exhibits large fragrant bi-color flowers.
3. *Nemesia×hybrida* 'Fleurbac' exhibits two individual colors of bi-color flowers per individual plant.

4. *Nemesia×hybrida* 'Fleurbac' is an ornamental that is suitable for use as a border plant, in a patio container or hanging basket.
5. *Nemesia×hybrida* 'Fleurbac' is 15 cm. in height and 15 cm. in width at maturity.
6. *Nemesia×hybrida* 'Fleurbac' sets few seeds.
7. *Nemesia×hybrida* 'Fleurbac' exhibits medium-green leaves.
8. *Nemesia×hybrida* 'Fleurbac' is hardy to minus 6° Centigrade.

BRIEF DESCRIPTION OF THE DRAWINGS

The accompanying color drawings illustrate the overall appearance of the new *Nemesia* cultivar 'Fleurbac' showing the colors as true as it is reasonably possible to obtain in colored reproductions of this type. Colors in the drawings may differ from the color values cited in the detailed botanical description, which accurately describe the actual colors of the new variety 'Fleurbac'. The drawings are made of a 6-month-old plant grown in 1-liter containers under greenhouse conditions in Encinitas, Calif.

The drawing labeled as FIG. 1 depicts an individual whole plant growing in a 1-liter container.

Figure 1:
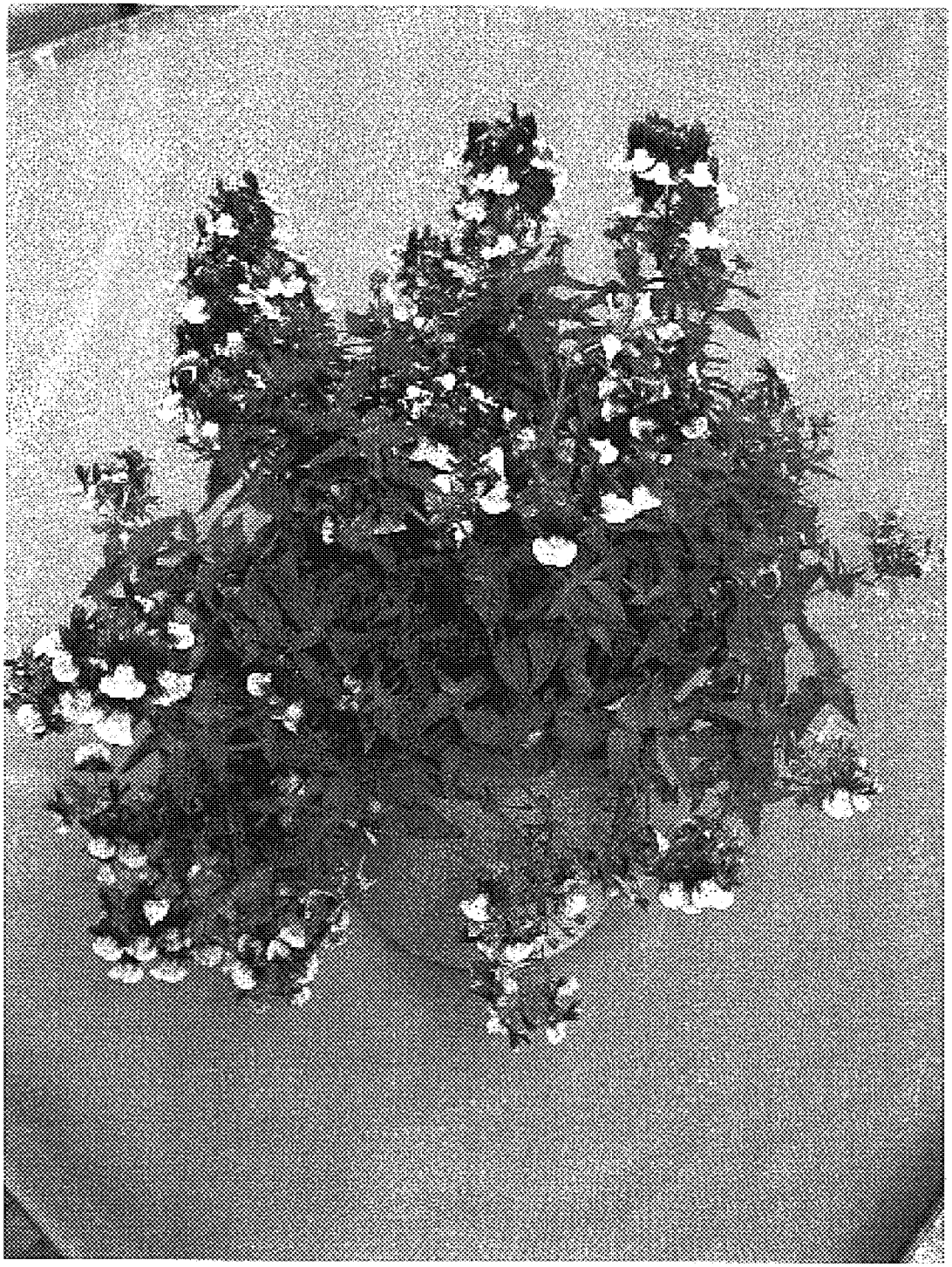
Figure 2:
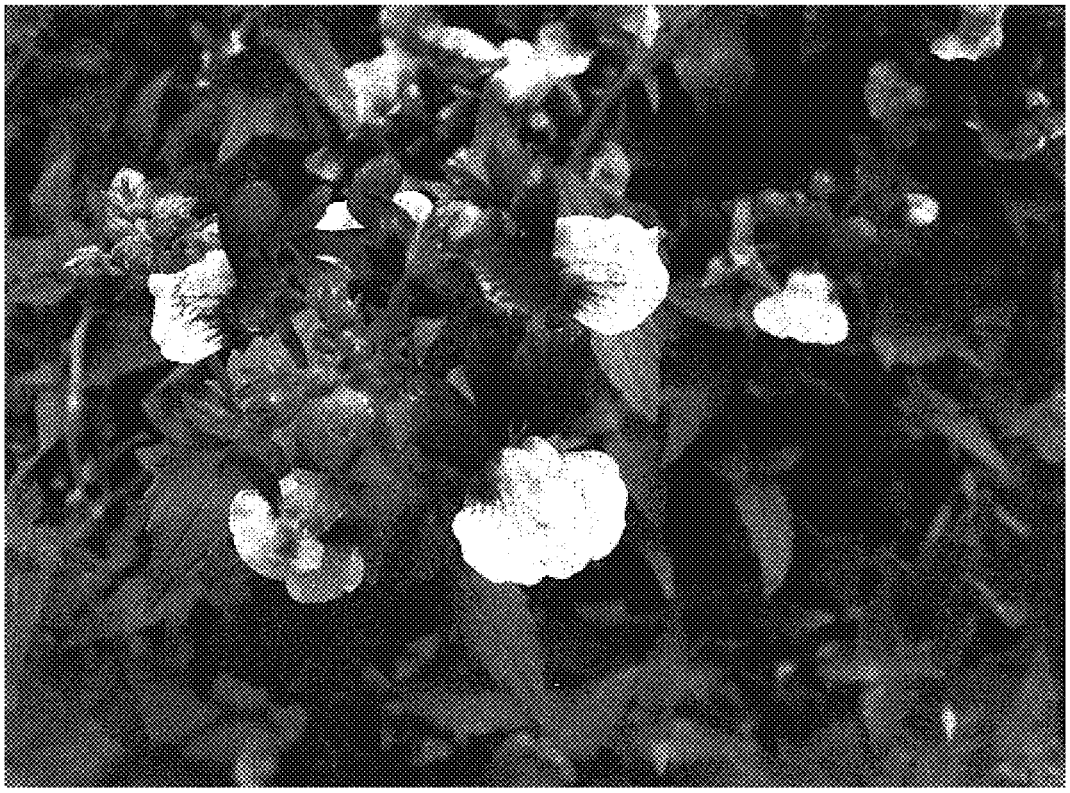

The drawing labeled as FIG. 2 depicts a close-up view, showing the bi-color flowers, and the two individual colors of bi-color flowers per individual plant.

All drawings were made using conventional techniques and although colors may appear different from actual colors due to light reflectance, they are as accurate as possible by conventional photography.

BOTANICAL DESCRIPTION OF THE PLANT

The following is a detailed description of the *Nemesia* plant named 'Fleurbac'. Data was collected in 2004 in Arroyo Grande, Calif. from 12 week-old plants grown under frost-protected greenhouse conditions. Phenotypic differences may be observed with variations in environmental, climatic, and cultural conditions. The color determinations are in accordance with the 2001 edition of The Royal Horticultural Society's Colour Chart, except where general color terms of ordinary dictionary significance are used. The growing requirements are similar to the species.

Botanical classification: *Nemesia×hybrida* 'Fleurbac'.
Genus: *Nemesia.*
Species:*×hybrida.*
Denomination: 'Fleurbac'.
Commercial classification: Ornamental.
Common name: *Nemesia.*
Suggested uses: For border plant, patio container or hanging basket.
Suggested commercial container size: 9 cm. or 1-liter commercial container.
Cultural needs: Full sun, moist, acidic well-draining soil.
Parentage: *Nemesia* 'Fleurbac' is a hybrid that resulted from the cross-pollination of the following parent plants:
*Seed parent.*—*Nemesia×hybrida* seedling 203.
*Pollen parent.*—*Nemesia×hybrida* seedling 200 (named 'Celine').
Propagation: Softwood cuttings.
Growth habit: Upright, compact habit.
Vigor: Vigorous.
Plant dimensions: Average dimensions of a plug are 7 cm. in height and 5.50 cm. in width. Dimensions at maturity are 15 cm. in height and 15 cm. in width.
Type: Perennial or annual, according to growing environment.
Seasonal interest: Bi-color flowers and two individual colors of bi-color flowers per individual plant.
Time to initiate roots: Approximately 14 days are needed to develop roots on initial cuttings.
Temperatures to initiate rooting: The air temperature that is recommended for rooting is 16° Centigrade and the soil temperature that is recommended for rooting is 24° Centigrade.
Crop time: From 5 to 8 weeks are needed to produce a finished 9 cm. container plant from a rooted cutting, and 2–3 months are needed to produce a finished 1-liter container plant from a rooted cutting.
Root system: Fine.
Hardiness: Hardy to minus 6° Centigrade.
Disease and pest susceptibility: 'Fleurbac' is susceptible to viruses and whitefly.
Special growing requirements:
*Pruning.*—Pinch back when potted from plug to commercial container.
*Soil.*—70% medium grade peat, 10% coarse peat and 20% 12 mm. bark.
*Light.*—Normal daylight.
Growing problems: None known to the inventor.
Stem:
*Stem shape.*—Quadrate.
*Stem length.*—4.25 cm. in length.
*Stem diameter.*—2.5 mm. in diameter.
*Stem surface.*—Glabrous with a longitudinal furrow on two sides.
*Stem color.*—138A.
*Pubescence.*—None observed.
*Stem texture.*—Soft and flexible.
*Internode length.*—2 cm. between nodes.
*Branching habit.*—Ascending and freely branching.
Foliage:
*Leaf arrangement.*—Opposite.
*Type.*—Evergreen.
*Leaf shape.*—Ovate.
*Average quantity of leaves per plug.*—An average of 25 leaves per plug.
*Leaf division.*—Simple.
*Apex.*—Acute.
*Base.*—Rounded.
*Margins.*—Crenate.
*Surface.*—Glabrous.
*Leaf pubescence.*—None observed.
*Leaf appearance* (*abaxial and adaxial surfaces*).—Matte appearance.
*Leaf length.*—Individual leaves range from 6 mm. to 2.25 cm. in length on an individual plug.
*Leaf width.*—Individual leaves range from 3 mm. to 1.25 cm. in width on an individual plug.
*Leaf color* (*adaxial surface*).—138A.
*Leaf color* (*abaxial surface*).—138B.
*Leaf attachment.*—Petiolate.
*Petiole shape.*—Sulcate.
*Petiole surface.*—Glabrous.
*Petiole dimensions.*—3 mm. in length and less than 1.25 mm. in diameter.
*Petiole color.*—138B.

*Vein pattern.*—Pinnate with mid-vein depressed on adaxial surface and protruding on abaxial surface.
*Vein color* (*adaxial and abaxial surfaces*).—138C.

Flowers:
*Flowering season.*—Spring and summer and fall.
*Fragrance.*—Perfume scent.
*Self-cleaning or persistent.*—Self-cleaning.
*Inflorescence dimensions.*—4 cm. in length and 4 cm. in width.
*Type of inflorescence.*—Terminal racemes.
*Quantity of flowers.*—An average of 6 flowers per plug.
*Peduncle dimensions.*—3 cm. in length and 2 mm. in diameter.
*Peduncle shape.*—Quadrate.
*Peduncle surface.*—Glabrous with longitudinal furrow on two sides.
*Peduncle color.*—138B.
*Pedicel dimensions.*—9 mm. in length and less than 0.50 mm. in diameter.
*Pedicel shape.*—Closest to cylindrical with one longitudinal furrow.
*Pedicel surface.*—Glabrous.
*Pedicel color.*—138B.
*Bud shape.*—Oval.
*Bud color.*—Colors 150D and 138A are individually present on an individual bud.
*Bud dimensions.*—4 mm. in diameter and 5 mm. in length.
*Quantity of buds.*—A range of 6–8 individual buds are present on an individual plug.
*Flower shape.*—Personate.
*Flower dimensions.*—1.50 cm. in diameter and 1 cm. in depth.
*Flower color* (*adaxial and abaxial surfaces*).—A mix of individual colors 79A, N74A, 77B, 155B and 3A are present on the bi-color flowers of an individual plant.
*Corolla tube dimensions.*—8 mm. in length and 3 mm. in diameter.
*Corolla tube color* (*inner and outer surfaces*).—Colors 77B and 155B are individually present on both the inner and outer surfaces of an individual corolla tube.
*Palate color* (*eye of flower*).—Adaxial surface is 3A and abaxial surface is 3D.
*Palate dimensions.*—3 mm. in length and 5 mm. in width.
*Nectary color.*—3A.
*Nectary dimensions.*—3 mm. in width and 6 mm. in length.
*Nectary surface.*—Lanate.
*Upper lip dimensions.*—1.50 cm. in width and 1 cm. in length.
*Upper lip color* (*adaxial and abaxial surfaces*).—Individual colors 79A, N74A, and 77B are present on the upper lip of flowers on an individual plant.
*Lower lip dimensions.*—1.50 cm. in width and 0.75 cm. in length.
*Lower lip color* (*adaxial and abaxial surface*).—155B and 3A.
*Upper lip margins.*—Lobed and entire.
*Lower lip margin.*—Entire.
*Number of lobes* (*upper lip*).—Four lobes in number.
*Fused or unfused* (*upper lip*).—Lobes basally fused.
*Lobe dimensions* (*upper lip*).—Each lobe is 5 mm. in width and 6 mm. in length.
*Upper lip apices.*—Each lobe exhibits a rounded apex.
*Lower lip apex.*—Closest to emarginate.
*Upper lip surfaces* (*adaxial and abaxial*).—Glabrous.
*Lower lip surfaces* (*adaxial and abaxial*).—Glabrous.
*Calyx dimensions.*—3 mm. in length and 4 mm. in width.
*Calyx shape.*—Stellate.
*Sepals.*—Five in number.
*Sepal dimensions.*—2 mm. in depth and 1 mm. in width.
*Sepal surface.*—Pubescent.
*Sepal shape.*—Lanceolate.
*Sepal apex.*—Acute.
*Sepal margin.*—Entire.
*Sepals fused or unfused.*—Unfused.
*Sepal base.*—Cuneate.
*Sepal color* (*adaxial surface*).—138A.
*Sepal color* (*abaxial surface*).—138A.
*Lastingness of individual flower on the plant.*—An individual flower lasts 7–10 days.

Reproductive organs:
*Stamens.*—Four in number.
*Color of stamens.*—155A.
*Stamen dimensions.*—1 mm. in length and less than 0.25 mm. in diameter.
*Anther color.*—163C.
*Amount of pollen.*—Moderate.
*Pollen color.*—163C.
*Anther dimensions.*—Less than 0.50 mm. in length and less than 0.50 mm. in width.
*Pistil.*—One.
*Pistil color.*—144D.
*Pistil dimensions.*—1 mm. in length and 0.25 mm. in diameter.
*Ovary dimensions.*—0.50 mm. in height and 0.50 mm. in diameter.
*Ovary shape.*—Globular.
*Ovary position.*—Superior.
*Ovary color.*—144D.

Seed:
*Quantity of seed.*—'Fleurbac' sets few seeds, a range of 0–5.
*Appearance of seed.*—Flattened and winged.
*Seed color.*—200D and wing 156D.
*Seed dimensions.*—An average of 2 mm. in length and 0.75 mm. in width.

It is claimed:

1. A new and distinct cultivar of *Nemesia* plant named 'Fleurbac' as described and illustrated herein.

* * * * *